(12) United States Patent
De La Bruniere

(10) Patent No.: US 8,758,823 B2
(45) Date of Patent: Jun. 24, 2014

(54) METHOD FOR OBTAINING NON-WATER-SOLUBLE POWDERS HAVING ANTIMICROBIAL ACTIVITY, THE POWDERS THUS OBTAINED AND THE ANTIBACTERIAL USE THEREOF

(75) Inventor: Patrick De La Bruniere, Paris (FR)

(73) Assignee: Poly-Bio, Paris (FR)

( * ) Notice: Subject to any disclaimer, the term of this patent is extended or adjusted under 35 U.S.C. 154(b) by 0 days.

(21) Appl. No.: 13/456,557

(22) Filed: Apr. 26, 2012

(65) Prior Publication Data
US 2012/0263776 A1 Oct. 18, 2012

Related U.S. Application Data

(63) Continuation of application No. PCT/IB2010/054261, filed on Sep. 21, 2010.

(30) Foreign Application Priority Data

Oct. 27, 2009 (FR) ..................................... 09 05162

(51) Int. Cl.
*A61K 9/14* (2006.01)
(52) U.S. Cl.
USPC ........................................................ 424/489
(58) Field of Classification Search
None
See application file for complete search history.

(56) References Cited

FOREIGN PATENT DOCUMENTS

| JP | 7089907 A | 4/1995 |
|---|---|---|
| JP | 2003160412 A | 6/2003 |
| WO | 2008122698 A1 | 10/2008 |

OTHER PUBLICATIONS

International Search Report for PCT/IB2010/050694 issued May 17, 2010; 6 pages.
Okano Takayoshi: "Solidification of Disinfective Didecyldimethylammonium Chloride", Apr. 4, 1995; XP002517921; retrieved from Caplus; 2 pages.

*Primary Examiner* — Carlos Azpuru
*Assistant Examiner* — Casey Hagopian
(74) *Attorney, Agent, or Firm* — Additon, Higgins, Pendleton & Ashe, P.A.

(57) ABSTRACT

A method for obtaining non-water-soluble powders comprising antimicrobial activity and having quaternary ammonium salts adhered thereto. The invention also includes the powders thus obtained and the use thereof as antibacterial agents. The invention enables the production of non-soluble organic or inorganic powders having a particle size of 5 to 500 μm, having a quaternary ammonium salt adhered to the surface thereof and fixed on the surface. When deposited on textile materials, the powders enable bacterial and viral decontamination, by means of filtration, of polluted water or aqueous environments. Textile materials impregnated with powders according to the invention can be used in the production of breathing masks, protective garments or other items, in particular in a hospital environment. The antibacterial properties of the powders are at least twice as high as the antibacterial properties of the same quaternary ammonium salt used in isolation.

8 Claims, No Drawings

METHOD FOR OBTAINING NON-WATER-SOLUBLE POWDERS HAVING ANTIMICROBIAL ACTIVITY, THE POWDERS THUS OBTAINED AND THE ANTIBACTERIAL USE THEREOF

CROSS-REFERENCE TO PRIORITY APPLICATION(S)

This application is a continuation of the commonly assigned International Patent Application No. PCT/IB2010/054261 (filed Sep. 21, 2010), and the commonly assigned French Application No. 09 05 162 (filed Oct. 27, 2009, in the French Patent Office), both of which are hereby incorporated by reference in their entirety.

FIELD OF THE INVENTION

A subject of the invention is a method for obtaining non-water-soluble powders having antimicrobial activity, to which quaternary ammonium salts adhere. It also relates to the powders thus obtained and to their use as antibacterial agents.

BACKGROUND

Quaternary ammonium salts are known to have the power to destroy numerous bacteria or viruses. Thus, the unexamined Japanese patent published under number 7-089907 in the name of Osaka Pharmaceutical Co. Ltd. indicates that didecyl dimethyl ammonium chloride is an antimicrobial agent having a disinfectant action, a strong bactericidal action with a broad antibiotic spectrum.

Therefore, said molecules are widely used in formulations intended for hygiene in the home, in hospital or other environments.

In a standard fashion quaternary ammonium salts, which are water-soluble, are used in antimicrobial applications in liquid form. In order to be effective, these solutions must be used at a certain concentration and, like quaternary ammonium salts, are not fixed to solid supports; after use, they remain in the treated aqueous phase or are removed and can therefore create long-term pollution.

The preparation of antimicrobial agents comprising solidified didecyl dimethyl ammonium chloride is difficult given the properties of this product. It has also been sought to fix quaternary ammonium salts to supports in order to be able to recover them more easily after use.

A subject of the abovementioned Japanese patent application is a powdery or pasty product comprising a high level of didecyl dimethyl ammonium chloride, obtained by mixing didecyl dimethyl ammonium chloride and an alkali metal phosphate, dried at 100-130° C. This patent describes a method of solidification in which all of the mixture containing the didecyl dimethyl ammonium chloride is solidified. It also describes a method for producing a solid formulation containing at least 40% didecyl dimethyl ammonium chloride.

The Japanese patent application published under number 2003-160412 in the name of Asahi Denka Kogyo KK describes an antibacterial biodegradable powder obtained by the impregnation of a powder preferably consisting of silica gel, zeolite or activated carbon with a quaternary ammonium salt comprising at least one ester group and comprising in particular 3 other $C_1$ to $C_4$ alkyl radicals. The quaternary ammonium salt taken into consideration in this patent application is an ester, the quaternary nitrogen atom comprising an ester substituent of formula $[(C_{2-4}$ alkylene)-O$]_{1-5}$—COalkyl or $[(C_{2-4}$ alkylene)-O$]_{1-5}$—CO-alkenyl. This application relates to the obtaining of heatresistant, sustained-release forms, comprising an antimicrobial agent other than a tetraalkyl ammonium salt and in particular other than didecyl dimethyl ammonium chloride.

The patent FR 2891545 in the name of La Brunière describes polyamide powders to which quaternary ammoniums are chemically fixed via a diisocyanate, using the —NH— groups of the polyamide chains. The field of application of this patent is limited to the polyamides and to the quaternary ammonium molecules possessing an —OH or —NH$_2$ functional group for example, capable of reacting with an isocyanate.

The patent EP 0952168A of Toray Industries describes a method for obtaining a grafted copolymer formed by polymerization with grafting of structural units containing quaternary ammonium groups and the presence of a substituent consisting of halogen ions, sulphates, sodium hydroxides and carboxylic acids. This technique requires the utilization of a monomer comprising a halogen atom and is more generally limited to grafting onto thermoplastic polymers.

The problem that the invention proposes to solve is to have an insoluble powdery material containing a powder readily available commercially, which material attracts bacteria by physical routes by fixing them on both sides, and has antibacterial properties leading to the destruction of the bacteria. The invention also proposes to solve the problems encountered by wearers of masks comprising filters the antibacterial materials of which, used in their composition, are carried towards the respiratory tracts of the mask wearer and cause respiratory problems.

None of the known materials makes it possible to achieve this objective, namely to obtain such a powder by such a method nor, moreover, does it make it possible to obtain the surprising and unexpected results that the powder according to the invention makes it possible to obtain.

SUMMARY OF THE INVENTION

A subject of the invention is a method for preparing non-water-soluble powders having an antibacterial activity, to the surface of which quaternary ammonium salts adhere, this method comprising the following stages:
  impregnation or wetting of a base powder having a particle size comprised between 5 µm and 500 µm with a solution of a quaternary ammonium salt the substituents of which are $C_1$-$C_{15}$ alkyl derivatives,
  treatment of the powder thus impregnated with a saline solution of an acid the molecule of which is a phosphate derivative and the molecular weight of which is greater than 100 g/mol
  drying the powder.

According to an embodiment of the method of the invention, the weight of quaternary ammonium salt in the form of chloride relative to the base powder used is 0.2 to 5% of the weight of said powder.

According to another embodiment of the method of the invention, the base powder is an inorganic powder.

According to a further embodiment of the method of the invention, the inorganic powder consists of one of the products in the following list: silica, natural or synthetic silicates, natural or synthetic insoluble carbonates, tricalcium phosphates.

According to yet another embodiment of the method of the invention, the inorganic powder consists of infusorial earths such as Kieselguhr or Celite.

According to another embodiment of the method of the invention, the base powder consists of thermoplastic or thermosetting polymers. These polymers can be obtained in the form of powders either by grinding, or by polymerization.

According to yet another embodiment of the method of the invention, the thermoplastic or thermosetting polymers consist of products belonging to the list comprising the polyamides, polyolefins, polystyrenes, polyacrylates.

According to yet another embodiment of the method of the invention, the quaternary ammonium used is a didecyl dimethyl ammonium salt.

According to a form of implementation of the method of the invention, the saline solution used is a polyphosphate, a tripolyphosphate or a pyrophosphate.

Variants of this method can be used as shown by the following examples, in particular impregnation and reaction can take place simultaneously. An additional treatment consists of removing the salt, in general sodium chloride or bromide formed during the reaction, by washing.

A subject of the present invention is also the powders resulting from the implementation of this method.

According to an embodiment form of these powders, the latter consist of powders to the surface of which molecules of didecyl dimethyl ammonium pyrophosphate, polyphosphates or tripolyphosphates adhere and which have a particle size comprised between 5 μm, and 500 μm.

According to another embodiment form of these powders, the latter are formed by base powders formed by inorganic materials or by thermoplastic or thermosetting polymers.

These base powders can be constituted by inorganic materials, such as, for example, silica, natural or synthetic silicates, infusorial earths such as Kieselguhr or Celite, natural or synthetic insoluble carbonates, tricalcium phosphates, preferably Kieselguhr, without this list being limitative.

They can also be constituted by polymers such as: polyamides, polyolefins, polyacrylates, polycarbonates, polystyrenes, thermoplastic or thermosetting polymers, preferably polyamides, without this list being limitative.

A subject of the present invention is also the use of powders according to the invention in antibacterial applications requiring a disinfectant action, a strong bactericidal action and a broad antibiotic spectrum.

A subject of the present invention is moreover textile materials to which the powders according to the invention are fixed by any suitable technique, for example by hot calendering.

These textile materials can be used for numerous applications in the hospital field: respiratory masks, surgical drapes, gowns. In daily life, masks and protective garments, undergarments can be formed from these treated textile materials. These wovens or non-wovens impregnated with said powders can be used for the manufacture of filters intended for the purification of air or aqueous media.

DETAILED DESCRIPTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

It is particularly advantageous to use the textile materials thus obtained for the manufacture of hospital textiles, in particular hospital masks. In fact, due to the water vapour contained in the respiratory flows, the use of masks which comprise non-fixed quaternary ammonium salts in the material of which they are formed, causes the entrainment of quaternary ammonium salts, and therefore breathing difficulties for the mask wearer who would inhale these salts.

In order to obtain antibacterial wovens or non-wovens, it would not be effective to impregnate said wovens or non-wovens with a commercial solution of a quaternary ammonium salt, such as didecyl dimethyl ammonium chloride, and dry them. In fact, the antibacterial property would disappear by entrainment with the first washing and, in the case of respiratory masks, the ambient humidity or moisture in the breath would dissolve the quaternary ammonium salt, which could then be entrained in aerosol form, and would risk being inhaled.

Furthermore, the fact that the quaternary ammonium salt adheres to the powder and due to the non-soluble character of said powder, the powders retain the quaternary ammonium salts on their surface and these quaternary ammonium salts cannot therefore be found in the environment.

These powders can also serve to filter aqueous media in order to reduce or destroy the microbial populations.

The weight of quaternary ammonium salt in the form of chloride relative to the base powder used is preferably from 0.2 to 5% of the weight of said powder, and, at this level, the final powder obtained, the subject of the invention, retains the same particle size and the same insolubility as the initial powder. In fact the quaternary ammonium salts resulting from the reaction between the quaternary ammonium chloride and the phosphate derivative consist of salts of didecyl dimethyl ammonium pyrophosphate, polyphosphates or tripolyphosphates.

The powders used according to the invention have a particle size preferably of 5 to 500 microns.

It has been found that this method leads to a non-water-soluble adherent film being obtained on the surface of the powder used. This film, given the small quantity of quaternary ammonium salt utilized, preferably from 0.5 to 5% by weight of powder, changes neither the appearance nor the physical characteristics of said powder, particle size, porosity and specific surface area in particular.

The type of action of the powders according to the invention combines the power of retention of bacteria of the base powders used for their manufacture with the bactericidal power of the insoluble quaternary ammonium salt, such as quaternary ammonium polyphosphate, tripolyphosphate or pyrophosphate, which adheres to the surface of the powder according to the invention.

In fact, the base powders used, in particular the POLY-BIO's BIONYL®-type polyamide powders, with no particular treatment, have a power of retention of bacteria which can reach $10^9$ CFU per gram of powder. This phenomenon is explained by the structure of the particles of this type of powder, which possess multiple pores with an average dimension equal to 1 micron, suitable for the collection of bacteria. Consequently, those powders with a particle size of 5 to 50 microns, have a low bulk density of 0.3 to 0.45 g/ml, and a specific surface area of approximately 5 $m^2$ to 15 $m^2$/g.

The bacteria fixed to the base powders are still alive. When a quaternary ammonium pyrophosphate, tripolyphosphate or polyphosphate, for example, even at a very low dose, is fixed to the surface of this type of base powder, the powder obtained, according to the invention, retains its power to attract bacteria, but the latter are then destroyed upon contact with the surface of the powder.

This type of action is completely different from that of the soluble quaternary ammonium salts used in aqueous solution, as, in this case, the destruction of the bacteria results mainly from Brownian motion.

It is entirely surprising and unexpected that the invention allows the use of such low quantities of quaternary ammonium salts to lead to the results and advantages produced by the present invention.

Furthermore, as regards textile materials, because said powder is non-water-soluble, its antibacterial activity is maintained during successive filtrations and dispersions in polluted aqueous phases. It is therefore possible to use this type of powder for the decontamination of water by filtration without leaving traces of quaternary ammonium salt in the treated water and using only quantities of quaternary ammonium completely different from those that would have to be used if this same water had been treated directly with this same quaternary ammonium salt in solution. This surprising and unexpected result confirms the innovative nature of the powders according to the invention. Moreover as shown below, the thus-treated textile materials retain their antibacterial properties after a certain number of washings which allows a long-term use of the articles formed from these textile materials.

An essential feature of the invention is the exceptional antibacterial activity of the powders obtained.

In fact, in order to explain this phenomenon, the antibacterial activity is measured in the same inoculum the bacterial concentration of which has been determined in CFU/ml.

On the one hand, for a powder according to the invention dispersed in this inoculum in a fixed dose of x grams per 100 ml of said inoculum for example, these x grams contain a quantity of quaternary ammonium fixed at the time of the manufacture of said powder of y grams (y being of the order of 0.2% to 5% of x).

Tests have demonstrated that the dispersion of the powder according to the invention is at least twice as active as in the case of the use of quaternary ammonium in solution.

Other aims and advantages will become apparent on reading the following examples, given in non-limitative manner.

Example No. 1

Raw Materials:

| | |
|---|---|
| ARQUAD ® 210-50 | 250 ml |
| BIONYL ® 650 | 10 kg |
| Sodium tripolyphosphate | 64 g |
| Water | 27 litres |

ARQUAD® 210-50 is the didecyl dimethyl ammonium chloride manufactured by AKZO NOBEL.

BIONYL® 650 is a polyamide 6 powder with a particle size of 50μ obtained from Poly-bio. The specific surface area is 5 m² per gram of powder.

Procedure:
in a stirred reactor, 10 kg of BIONYL® 650 are dispersed in 27 liters of water at room temperature,
250 ml of ARQUAD® 210-50 is progressively added while stirring for approximately 10 minutes in order to homogenize the mixture,
without stopping the stirring, a solution of 64 g of sodium polyphosphate in 3 liters of water is added,
heating at 80° C. and stirring for approximately 30 minutes,
removing the remaining water, optionally under vacuum, and heating at 100° C. until a dry fluid powder is obtained.

Monitoring the powder obtained shows that the particle size and the specific surface area of the polyamide have remained identical.

Test of the Activity of the Powder Obtained:

7.2 g of this dried powder containing 1.1% of didecyl dimethyl ammonium are introduced into 100 ml of an inoculum containing 109 CFU of *Escherichia coli* per ml and dispersed by stirring.

The following results were obtained:
After

| | |
|---|---|
| 5 minutes of stirring | $10^6$ CFU/ml |
| 10 minutes of stirring | $10^2$ CFU/ml |
| 20 minutes of stirring | 0 CFU/ml |

Example No. 2

Raw Materials:

| | |
|---|---|
| ARQUAD ® 210-50 | 25 ml |
| BIONYL ® 615 | 1 kg |
| Sodium tripolyphosphate | 6.4 g |
| Water | 2.7 litres |

BIONYL® 615 is a high-porosity polyamide 6 powder with a particle size of 15 microns having a specific surface area of 12 m²/g manufactured by the company POLY-BIO.

The procedure is identical to that of Example No. 1.

The powder obtained is subjected to a bactericidal activity test according to standard UNE-EN 1040 on the bacterium *Staphylococcus aureus*.

At a concentration of 0.05% of powder in the inoculum tested, the bacterial reduction is greater than 5 Log.

Given the level of quaternary ammonium in this powder, this corresponds to approximately 6 ppm of ARQUAD® 210-50.

In order to obtain the same result, AKZO NOBEL (Guideline formulation on ARQUAD 210-50) recommends a concentration of 12 to 16 ppm for this quaternary ammonium chloride in aqueous solution.

Example No. 3

Non-Woven Impregnated with Powder:
Raw Materials:
BIONYL® 650 treated according to Example No. 1
Non-woven of approximately 30 g/m² comprising 70% polypropylene fibres and 30% polyethylene fibres.

The technique of scattering then fixing the powder onto the non-woven developed by the company FIBROLINE according to which the powder is fixed by surface melting of the fibre at a temperature much lower than the melting point of polyamide by calendering at a temperature of 120° C.

Two weights per unit area of powder have been produced, namely:
20 g/m² of powder
40 g/m² of powder The impregnated non-wovens obtained are tested according to standard JIS L 1902 used for monitoring the antibacterial activity of textile materials.

In order to comply with this standard, the coefficient used must be greater than zero.

The coefficient obtained for the 20 g/m² non-woven is 0.023 and 1.3 for 40 g/m².

The bacteria tested are: *S. aureus, E. coli, Pseudomonas aeruginosa, Klebsiella pneumoniae*.

This makes the use of these non-wovens possible in hospital environments. In fact, the possibility of subjecting articles formed from this type of material to several washings without them losing their antibacterial property is particularly useful from the economic point of view. Furthermore, the fact that the ammonium salts fixed to these textile materials are insoluble, makes articles formed from these textile materials particularly advantageous for, among other things, the manufacture of masks, in particular hospital masks. The insolubility of the powders used prevents them being solubilized in the respiratory flows and causing breathing difficulties to the individuals wearing them.

Example No. 4

Raw Materials:

BIONYL® 650+Water+50% BARDAC® 22 solution+Sodium polyphosphate.

BARDAC® 22 obtained from LONZA is a molecule comprising a quaternary ammonium chloride. It consists of 50% active quaternary didecyl dimethyl ammonium chloride. This product is soluble in water.

100 g of BIONYL® 650 and approximately 200 ml of water are introduced into a one-liter flask.

The mixture is stirred in order to wet it thoroughly. 2.5 g of BARDAC® 22 is added under stirring. Without stopping the stirring, a solution formed by 0.64 g of sodium polyphosphate in 50 ml of water is introduced into the same flask. The flask is placed in a rotary evaporator in order to evaporate all of the water over approximately 1 hour.

The final powder obtained is tested to determine its antibactericidal capacity. In order to do this, an inoculum originating from waste water and comprising $10^5$ CFU/ml is used.

The powder is first washed 5 times by mixing 10% in distilled water and subjected to successive filtrations. The washed powder is introduced into the inoculum at 10% by weight. After stirring for two minutes, the bacteria have completely disappeared.

Example No. 5

Raw Materials:

BIONYL® 608, water, BARDAC® 22, Sodium polyphosphate.

BIONYL® 608 is a polyamide 6 powder with a particle size of 8 microns obtained from POLY-BIO. Its high porosity confers upon it a significant power of retention of bacteria.

By way of example, dispersed at 10% by weight in an inoculum of *E. coli* at $10^8$ CFU/ml, this powder absorbs approximately $10^9$ bacteria per gram of powder.

The powder obtained is referenced BIONYL® 608 F1P1.

40 g of BIONYL® 608 F1P1 powder was washed 5 times, each time with 400 ml of water for two hours at ambient temperature. Between two wettings, the powder was filtered and dried each time.

| Contact time | Colonies present (germs/1) | Reduction in log |
|---|---|---|
| Control inoculum | $10^5$ to $10^6$ germs/litre | |
| Not washed | 0 | 6 |
| 1$^{st}$ washing | 0 | 6 |
| 2$^{nd}$ washing | 0 | 6 |
| 3$^{rd}$ washing | 0 | 6 |
| 4$^{th}$ washing | 10 | 5 |
| 5$^{th}$ washing | 10 | 5 |

It is found that after three washings the activity of the powder according to the invention has not varied and that even after 5 washings the reduction in activity is only 1 Log.

Example No. 6

Raw Materials:

WR GRACE SP 537-11092 silica, water, BARDAC® 22, sodium tripolyphosphate.

The silica used is a powder with a particle size of 100 to 200 microns.

100 g of silica, 200 ml of water and 2.5 g of BARDAC® 22 are introduced into a one-liter flask.

By stirring, a kind of paste is obtained, to which a solution of 0.64 g of sodium tripolyphosphate in 50 ml of water is added. After stirring for 10 minutes the content of the flask is placed in a rotary evaporator. After drying, it must be lifted off in order once again to obtain a homogeneous powder.

The final powder obtained is referenced BIOSIL F1P1.

By following the same procedure but using sodium polyphosphate a powder referenced BIOSIL F1P2 is obtained.

Using the previous the inoculum under the same conditions, the bacterial reduction is complete in 10 minutes with either BIOSIL F1P1 or BIOSIL F1P2.

Example No. 7

Monitoring of Wine-Making

The monitoring of wine-making is carried out on a Cramant Champagne wine juice obtained by pressing on a plate filter. The juice is clear and rich in sugars. This juice is normally treated with potassium sulphite in order to select the fermentation medium.

A sample of juice, referenced E1, is taken before sulphiting and before alcoholic fermentation. Two samples E2 and E3 are taken at hourly intervals at the end of alcoholic fermentation. Sample E2 was brought into contact with 5% BIONYL 608 F1P1 and sample E3 with 5% BIONYL 650 F1P1. The samples are stirred to allow the powder to be kept in suspension. The following table summarizes the results obtained. The figures shown are in CFU/ml.

| Reference | Bacteria | Yeasts | Moulds |
|---|---|---|---|
| E1 | $10^3$ | $10^5$ | 0 |
| E1 BIONYL 608 F1P1 | 0 | $10^3$ | 0 |
| E2 | 0 | $10^5$ | 0 |
| E2 BIONYL 608 F1P1 | 0 | $10^3$ | 0 |
| E3 | $10^3$ | $10^5$ | Significant |
| E3 BIONYL 650 F1P1 | $10^3$ | 0 | 0 |

The measurements were carried out with MERCK Cult Dip. BIONYL 608 F1P1 showed its effectiveness in controlling the fermentation population before alcoholic fermentation, which is necessary for all types of wine for in order to prevent malolactic fermentation, which is not wanted for white wines and champagnes. BIONYL 608 F1P1 can therefore be advantageously substituted for the standard bisulphite treatment.

Example No. 8

Raw Materials

CELITE 650, water, BARDAC 22, sodium tripolyphosphate.

CELITE 650 is an infusorial earth of the same kind as KIESELGUHR, having a particle size of approximately 100 microns.

Procedure:

10 kg of CELITE 650 powder and 25 liters of water are introduced into a stirred reactor.

The mixture was stirred to wet the powder and 1.05 kg of BARDAC 22 was added without stopping the stirring.

Once homogenization was achieved, a solution formed by 252 g of polyphosphate in 6 l of water is added to the stirred mass.

During this operation, the oily phase which forms little by little is absorbed by the Celite powder. When the medium is again homogeneous, it is placed in a rotary evaporator to remove the water while stirring.

The powder obtained is called BIOSIL 650 F1P1.

Monitoring of the activity of BIOSIL 650 F1P1:

10 g of BIOSIL 650 F1P1 is dispersed and stirred in 100 ml of an inoculum the bacterial load of which is expressed in CFU/ml.

This same test is carried out on the BIONYL 608 prepared in Example 5. The weight ratio of quaternary ammonium is 1% in the case of the BIONYL 608F1P1 and 4% in the case of the IONYL 608F1P1, therefore 4 times greater.

The table below summarizes the results obtained:

| Reference | Bacteria in CFU/ml | Bacterial reduction in Log |
|---|---|---|
| Initial inoculum | $10^5$ to $10^6$ germs/litre | |
| BIOSIL 650 at 10 min | 0 | 6 |
| BIONYL 608 F1P1 at 2 min | 0 | 6 |

It is found that BIONYL 608 F1P1 allows complete destruction of the germs in two minutes whereas BIOSYL 650 possessing a weight load of quaternary ammonium 4 times higher requires 10 minutes of treatment for the same result. This demonstrates the significant ability of BIONYL 608 powder (having served as a basis for the manufacture of the BIONYL 608 F1PA powder) to absorb bacteria.

The invention claimed is:

1. A method for preparing non-water-soluble powders having antibacterial activity, to a surface of which quaternary ammonium salts adhere, the method comprising the following stages:
   impregnation or wetting of a base powder having a particle size comprised between 5 µm and 500 µm with a solution of a soluble quaternary ammonium salt comprising substituents selected from C1-C15 alkyl derivatives;
   treatment of the powder thus impregnated with a saline solution of an acid which is a phosphate derivative with a molecular weight greater than 100 g/mol; and
   drying the powder;
   wherein the base powder is selected from the group consisting of an inorganic powder, thermoplastic polymers and thermosetting polymers.

2. The method according to claim 1, wherein the quaternary ammonium salt is a chloride and is used in a quantity relative to the base powder of 0.2 to 5% by weight to the weight of said powder.

3. The method according to claim 1, wherein the inorganic powder is selected from the group consisting of silica, natural or synthetic silicates, natural or synthetic insoluble carbonates, and tricalcium phosphates.

4. The method according to claim 1, wherein the inorganic powder is comprised of infusorial earths.

5. The method according to claim 1, wherein the thermoplastic or thermosetting polymers are selected from the group consisting of polyamides, polyolefins, polystyrene, and polyacrylates.

6. The method according claim 1, wherein the quaternary ammonium salt is a didecyl dimethyl ammonium salt.

7. The method according to claim 1, wherein the saline solution is selected from the group consisting of a polyphosphate, a tripolyphosphate and a pyrophosphate.

8. The method according to claim 4, wherein the infusorial earth is selected from the group consisting of Kieselguhr and Celite.

* * * * *